US007682794B2

(12) United States Patent
Varki et al.

(10) Patent No.: US 7,682,794 B2
(45) Date of Patent: Mar. 23, 2010

(54) METHODS FOR DETECTING AND ANALYZING N-GLYCOLYLNEURAMINIC ACID (NEU5GC) IN BIOLOGICAL MATERIALS

(75) Inventors: Ajit Varki, La Jolla, CA (US); Pam Tangvoranuntakul, San Francisco, CA (US); Nissi Varki, La Jolla, CA (US); Elaine Muchmore, La Jolla, CA (US); Pascal Gagneux, San Diego, CA (US); Sandra Diaz, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 10/565,742

(22) PCT Filed: Jul. 14, 2004

(86) PCT No.: PCT/US2004/022415

§ 371 (c)(1),
(2), (4) Date: Jun. 25, 2007

(87) PCT Pub. No.: WO2005/010485

PCT Pub. Date: Feb. 3, 2005

(65) Prior Publication Data

US 2007/0275409 A1      Nov. 29, 2007

Related U.S. Application Data

(60) Provisional application No. 60/487,533, filed on Jul. 15, 2003.

(51) Int. Cl.
*G01N 33/53* (2006.01)
(52) U.S. Cl. .................. 435/7.1; 435/90.1; 435/90.2
(58) Field of Classification Search .................. None
See application file for complete search history.

(56) References Cited

U.S. PATENT DOCUMENTS

| 4,695,198 | A | 10/1990 | Yamasaki et al. |
| 5,045,532 | A | 9/1991 | Valle et al. |
| 5,059,680 | A | 10/1991 | Davis et al. |
| 2002/0192231 | A1* | 12/2002 | Zhu et al. ............ 424/185.1 |

FOREIGN PATENT DOCUMENTS

EP          0316818         11/1988

OTHER PUBLICATIONS

Brinkman-Van Der Linden, Els C. M.; E. R. Sjoberg; L. R. Juneha; P. R. Crocker; N. Varki; and A. Varki; "Loss of N-Glycolylneuraminic Acid in Human Evolution"; The Journal of Biological Chemistry; Mar. 24, 2000, vol. 275, No. 12. pp. 8633-8640.
Bardor, Muriel; D. H. Nguyen; S. Diaz; and A. Varki; "Mechanisms of Uptake and Incorporation of the Non-human Sialic Acid N-Glycolylneuraminic Acid into Human Cells"; The Journal of Biological Chemistry, Feb. 11, 2005, vol. 280, No. 6, pp. 4228-4237.
Sonnenburg, Justin L.; H. van Halbeek; and A. Varki "Characterization of the Acid Stability of Glycosidically Linked Neuraminic Acid"; The Journal of Biological Chemistry; May 17, 2002; vol. 277, No. 20, pp. 17502-17510.
Oetke, Cornelia; S. Hinderlich; R. Brossmer; W. Reutter; M. Pawlita; and O. T. Keppler; "Evidence for efficient uptake and incorporation of sialic acid by eukaryotic cells"; Eur. J. Biochem.; 2001; 265; pp. 4553-4561.
Devine, Peter L.; B. A. Clark; G. W. Birrell; G. T. Layton; B. G. Ward; P. F. Alewood; and I. F. C. McKenzie; Cancer Research; Nov. 1, 1991; 51, pp. 5826-5836.
Marquina, Gilda; H. Waki; L. E. Fernandez; K. Kon; A. Carr; O. Valiente; R. Perez; and S. Ando; "Gangliosides Expressed in Human Breast Cancer"; Cancer Research; Nov. 15, 1996; 56; pp. 5165-5171.
Chou, Hsun-Hua; T. Hayakawa; S. Diaz; M. Krings; E. Indriati; M. Leakey; S. Paabo; Y. Satta; N. Takahata; A. Varki; "Inactivation of CMP-N-acetylneuraminic acid hydroxylase occurred prior to brain expansion during human evolution"; PNAS; Sep. 3, 2002; vol. 99, No. 18; pp. 11736-11741.
Chou, Hsun-Hua; H. Takematsu; S. Diaz; J. Iber; E. Nickerson; K. L. Wright; E. A. Muchmore; D. L. Nelson; S. T. Warren; and A. Varki; "A mutation in human CMP-sialic acid hydroxylase occurred after the *Homo-Pan* divergence"; Proc. Natl. Acad. Sci. USA.; Sep. 1998; vol. 95; pp. 11751-11756.
Varki, Ajit; "Sialic acids such as ligands in recognition phenomena" The FASEB Journal; Mar. 1997; vol. 11, pp. 248-255.
Muchmore, Elaine A..; S. Diaz; and A. Varki; "A Structural Difference Between the Cell Surfaces of Humans and the Great Apes"; American Journal of Physical Anthropology; Jun. 10, 1998; 107; pp. 187-198.
Sjoberg, Eric R.; L. D. Powell; A. Klein; and A. Varki; "Natural Ligands of the B Cell Adhesion Molecule CD22β can be Masked by 9-*O*-Acetylation of Sialic Acids"; The Journal of Cell Biology; Jul. 1994; Voo. 126, No. 2., pp. 549-562.
Collins, Brian E.; T. J. Fralich; S. Itonori; Y. Ichiawa; and R. L. Schnaar; "Conversion of cellular sialic acid expression from N-acetyl- to N-glycolylneuraminic acid using a synthetic precursor, N-glycolylmannosamine pentaacetate: inhibition of myelin-associated glycoprotein binding to neural cells" Glycobiology; 2000, vol. 10, No. 1, pp. 11-20.

(Continued)

*Primary Examiner*—Jacob Cheu
(74) *Attorney, Agent, or Firm*—Medlen & Carroll, LLP

(57) ABSTRACT

The present application is in the field of sialic acid chemistry, metabolism and antigenicity. More particularly, the present invention relates to the detection and analysis of the non-human sialic acid, N-glycolylneuraminic acid (Neu5Gc) in bio-logical materials, such as food and clinical specimens. Such detection and analysis is facilitated by the use of Neu5Gc specific antibodies. The present invention also relates to the detection of anti Neu5Gc antibodies in clinical samples, as well as the production of anti-Neu5Gc specific antibodies.

14 Claims, 7 Drawing Sheets

OTHER PUBLICATIONS

Bardor, Muriel, D. H. Nguyen; S. Diaz; and A. Varki; "Mechanism of Uptake and Incorporation of the Non-Human Sialic Acid N-glycolylneuraminic acid into Human Cells"; JBC Papers in Press, Manuscript M412040200; Nov. 12, 2004; 43 pages.

Bardor, Muriel; D. H. Nguyen; S. Diaz; and A. Varki; "Mechanism of Uptake and Incorporation of the Non-human Sialic Acid N-Glycolyneuraminic Acid into Human Cells"; The Journal of Biological Chemistry; Feb. 11, 2005; vol. 290, No. 6., pp. 4228-4237.

* cited by examiner

METHODS FOR DETECTING AND ANALYZING N-GLYCOLYLNEURAMINIC ACID (NEU5GC) IN BIOLOGICAL MATERIALS

CROSS-REFERENCE TO RELATED APPLICATIONS

This application claims priority from U.S. Provisional Application 60/487,533, which was filed on Jul. 15, 2003.

GOVERNMENT INTEREST

This invention was made with government support from the National Institutes of Health under grant number R01GM32373.

TECHNICAL FIELD

The present application is in the field of sialic acid chemistry, metabolism and antigenicity. More particularly, the present invention relates to the detection and analysis of the non-human sialic acid, N-glycolylneuraminic Acid (Neu5Gc) in biological materials, such as food and clinical specimens. The present invention also relates to the detection of Neu5Gc antibodies in clinical samples, as well as the production of anti-Neu5Gc-specific antibodies.

BACKGROUND

All cells are covered with a dense and complex array of sugar chains. Sialic acids (Sias) are a family of nine-carbon sugars that are typically present at the outermost units of these sugar chains. By virtue of their terminal position, sialic acids act as binding sites for many exogenous and endogenous receptors such as the Influenza viruses and the Siglec family of endogenous proteins. Such sugars are thus useful drug targets for the prevention and treatment of infection. They are also involved in various biological and pathological processes such as neuronal plasticity and cancer metastasis. In many of these instances, the precise structures of the sialic acid and the residues it is attached to play critical roles. Thus, studying sialic acid functions is of great biological importance, and antibodies specific for sialic acids are valuable tools in elucidating their biological functions. More specifically, these antibodies would be useful to screen normal human tissues for traces of Neu5Gc, which may be incorporated from certain dietary sources (red meat and diary products), and may also be associated with certain disease states, such as cancer and heart disease.

Sialic acids are typically found as the outermost-units on the mammalian cellular glycocalyx, and on secreted glycoproteins. (Gottschalk, A. (1960), *The Chemistry and Biology of Sialic Acids*, University Press, Cambridge, U.K.; Rosenberg, A. and Schengrund, C. (1976), *Bilogy of Sialic Acids*, Plenum Press, New York, N.Y.; Schauer, R. (1982) *Adv. Carbohydr. Chem. Biochem.* 40:131-234; and Angata, T. and Varki, A. (2002) *Chem. Rev.* 102:439-470.) The most common Sias are N-acetylneuraminic acid (Neu5Ac) and N-glycolylneuraminic acid (Neu5Gc). Cellular Neu5Gc is generated by hydroxylation of the sugar nucleotide donor CMP-Neu-5Ac to CMP-Neu-5Gc, catalyzed by CMP-Neu5Ac hydroxylase (CMAH). (Shaw, L. and Schauer, R. (1988) *Biol. Chem. Hoppe-Seyler* 369:477-486; Kozutsumi, Y., Kawano, T., Yamakawa, T. and Suzuki, A. (1990) *J. Biochem.* (Tokyo) 108: 704-706; and Muchmore, E. A., Milewski, M., Varki, A., and Diaz, S. (1989) *J. Biol. Chem.* 264: 20216-20223.)

Although Neu5Gc is a major Sia in most mammals (including our closest evolutionary relatives, the great apes; Muchmore, E. A., Diaz, S. and Varki, A. (1998) *Am. J. Phys. Anthropol.* 107: 187-198), it is thought to be absent in healthy humans (Gottschalk, et. al.; Rosenberg, et al.; and Schauer, supra). Indeed, humans generate immune responses against intravenously administered molecules carrying Neu5Gc, e.g. the "serum sickness" reaction to equine anti-thymocyte globulin therapy (Higashi, H., Naiki, M., Matuo, S. and Okouchi, K. (1977), *Biochem. Biophys. Res. Comm.*, 79: 388-395; and Merrick, J. M., Zadarlik, K. and Milgrom, F. (1978), *Int. Arch. Allergy Appl. Immunol.* 57: 477-480). These findings are explained by a human-specific inactivating mutation in the CMAH gene that occurred 2.5-3 million years ago (Chou, H. H., Takematsu, H., Diaz, S., Iber, J., Nickerson, E., Wright, K. L., Muchmore, E. A., Nelson, D. L., Warren, S. T. and Varki, A. (1998), *Proc. Natl. Acad. Sci. USA* 95:11751-11756; Irie, A., Koyama, S., Kozutsumi, Y., Kawasaki, T. and Suzuki, A. (1998), *J. Biol. Chem.* 273:15866-15871; Varki, A. (2002), *Yearbook Phys. Anthropol.* 44:54-69; and Chou, H. H., Hayakawa, T., Diaz, S., Krings, M., Indriati, E., Leakey, M., Paabo, S., Satta, Y., Takahata, N. and Varki, A. (2002), *Proc. Natl. Acad. Sci. USA* 99:11736-11741).

Despite no known alternate pathway for Neu5Gc synthesis in humans, antibodies have been used to claim its presence in some human cancers and in human fetal meconium. (Hirabayashi, Y., Kasakura, H., Matsumoto, M., Higashi, H., Kato, S., Kasai, N. and Naiki, M. (1987), *Japan J. Cancer Res.* 78:251-260; Higashi, H., Hirabayashi, Y., Fukui, Y., Naiki, M., Matsumoto, M., Ueda, S. and Kato, S. (1985), *Cancer Res.* 45:3796-3802; Miyoshi, I., Higashi, H., Hirabayashi, Y., Kato, S. and Naiki, M. (1986), *Mol. Immunol.* 23: 631-638; Marquina, G., Waki, H., Fernandez, L. E., Kon, K., Carr, A., Valiente, O., Perez, R. and Ando, S. (1996), *Cancer Res.* 56: 5165-5171; Devine, P. L., Clark, B. A., Birrell, G. W., Layton, G. T., Ward, B. G., Alewood, P. F. & McKenzie, I. F. C. (1991), *Cancer Res.* 51:5826-5836; and Kawachi, S., Saida, T., Uhara, H., Uemura, K., Taketomi, T. and Kano, K. (1988), Int. Arch. Allergy Appl. Immunol. 85:381-383.) However, the specificity of the polyclonal antibodies used was not well defined.

One study using mAbs failed to detect Neu5Gc in human tumors and tissues (Furukawa, K., Yamaguchi, H., Oettgen, H. F., Old, L. J. and Lloyd, K. O. (1988), *J. Biol. Chem.* 263:18507-18512). However, these mAbs were specific for Neu5Gc only in the context of underlying structural motifs. Another mAb thought to be specific for Neu5Gc cross-reacts with some sulfated glycolipids (Vázquez, A. M., Alfonso, M., Lanne, B., Karlsson, K. A., Carr, A., Barroso, O., Fernández, L. E., Rengifo, E., Lanio, M. E., Alvarez, C., Zeuthen, J. and Pérez, R. (1995), *Hybridoma* 14:551-556). Meanwhile, some reports claim chemical proof for Neu5Gc in human tumors Marquina, et al., Devine, et al., supra, and Kawai T., Kato, A., Higashi, H., Kato, S. and Naiki, M. (1991), *Cancer Res.* 51:1242-1246). Overall, prior data is inconclusive about the frequency and distribution of Neu5Gc expression in tumors.

Human biosynthetic pathways could theoretically allow exogenous Neu5Gc to be metabolically incorporated (Varki A., et al., supra, and Oetke, C., Hinderlich, S, Brossmer, R., Reutter, W., Pawlita, M. and Keppler, O. T. (2001), *Eur. J. Biochem.* 268:4553-4561). Indeed, human cells cultured in fetal calf serum express cell surface Neu5Gc in small amounts (Muchmore, et al., and Furukawa, et al., supra). However, it is not known if this represents passive adsorption of serum glycoconjugates or metabolic incorporation. Although earlier studies claimed the absence of Neu5Gc from normal human tissues, a small HPLC peak was noted at the elution time of Neu5Gc in extracts from human organs (Muchmore, et al., supra). More recent studies as discussed elsewhere herein have established the pathway for uptake and incorporation of Neu5Gc by human cells.

Anti-Neu5Gc antibody levels in human sera have also been reported, primarily in patients with various diseases. The presence of such antibodies in normal individuals was considered to be rare. However, assays used in all previous studies lacked absolute specificity for Neu5Gc and also suffered from very high background signals. Thus, they lacked the sensitivity to detect low levels of anti-Neu5Gc antibodies and failed to be certain about the specificity of the reacting antibodies. For example, one study used high molecular weight glycoproteins (HMWG) extracted from bovine erythrocytes as a target without a true negative control, and arbitrarily defined a positive result as an absorbance value of more than 0.5. Thus, only sera with very high reactivity, such as those of patients with certain disease states, would have been identified as positive. Another study that also utilized HMWG as the target, without a true negative control, defined a positive result as the value obtained after subtracting the results obtained using non-coated wells from results obtained using HMWG coated wells. The propensity for serum proteins to bind non-specifically to non-coated wells would have also given a high background in this assay, again making it difficult to identify weakly positive-samples. In both assays the specificity of the reacting antibodies would also not be clearly defined, since cross-reactivity with other bovine molecules could occur.

Accordingly, the present invention relates to detection and analysis of Neu5Gc content of biological materials, such as food and human clinical samples. It also relates to the study of induced and natural antibodies that are specific for Neu5Gc, and their use in the study of Neu5Gc in the laboratory, as well as the detection of Neu5Gc antibodies in clinical specimens. The invention also relates to general methods for selecting anti-sialic acid specific antibodies.

SUMMARY OF THE INVENTION

The non-human sialic acid Neu5Gc is found in various food and can be taken up and incorporated into human tissues. This can be accomplished by a human antibody response to Neu5Gc. The presence of the antigen and the antibody in the same person could facilitate the occurrence of a variety of diseases. This invention relates to the detection and quantitation of Neu5Gc in food and clinical samples, as well as measurement of anti-Neu5Gc antibodies in order to make prognostic statements about the risk of various disease and to facilitate dietary recommendations. The invention also includes methods for specific production and detection of sialic acid-specific antibodies.

In one embodiment, the present invention is a method of determining % N-glycolylneuraminic acid (Neu5Gc) of a biological material comprising the steps of: (a) measuring the amount of N-acetylneuraminic acid (Neu5Ac) present in the material per given weight; (b) measuring the amount of Neu5Gc present in the material per given weight; and (c) calculating the % Neu5Gc of the sample, wherein % Neu5Gc is determined using the formula: % Neu5Gc=[(Neu5Gc)/(Neu5Ac+Neu5Gc)]×100. The biological material can be virtually any organic material suspected of containing Neu5Gc, such as a food sample (for example, red meat or a dairy product) or a clinical sample. The clinical sample may be from any animal source, such as a human. Human samples can be from any body fluid or tissue, such as urine, saliva, soft or hard tissue, urine, etc.

The Neu5Gc content of food is particularly important. As such the Neu5Gc content of food can be calculated on a "weight per serving" basis by multiplying the Neu5Gc content per weight by the serving size.

When the % Neu5Gc is measured in a clinical sample, it may also be important to monitor changes in the % Neu5Gc over time, especially in response to dietary changes.

In another embodiment, the invention is a method of purifying sialic acid-specific antibodies, comprising the steps of: (a) preparing antibodies to sialic acids; (b) contacting the antibodies from step (a) with a first solid phase to which a sialic acid having a side chain has been attached; and (c) contacting the antibodies that bound to the first solid phase with a second solid phase to which the sialic acid without the side chain has been attached. The sialic acid can be any member of the sialic acid family. Examples include N-acetylneuraminic acid, N-glycolylneuraminic acid, Ketodeoxynonulosonate (KDN) N-propanoylneuraminic acid, N-butanoylneuraminic acid, N-pentanoylneuraminic acid, N-hexanoylneuraminic acid, N-heptanoylneuraminic acid, N-oxooctanoylneuraminic acid, N-levulinolylneuraminic acid, N-homolevulinoylneuraminic acid, N-oxohexanoylneuraminic acid, N-oxoheptanoylneuraminic acid, and N-oxooctanoylneuraminic acid, as well as natural and synthetic derivatives of the foregoing sialic acids.

Although any method may be used to remove the sialic acid side chain either before or after attachment to the second solid phase, the use of periodate is preferred.

The present invention also includes a method of detecting anti-Neu5Gc specific antibodies in a biological material comprising the steps of: (a) determining the amount of anti-Neu5Ac antibodies present in the material; (b) determining the amount of anti-Neu5Gc antibodies present in the material; and (c) subtracting the amount of anti-Neu5Ac antibodies from the amount of anti-Neu5Gc antibodies to determine the amount of anti-Neu5Gc specific antibodies. The same types of biological materials described above can be assayed for the presence of anti-Neu5Gc antibodies.

In yet another embodiment, the present invention relates to a composition comprising an affinity purified antibody specific for binding N-glycolylneuraminic acid (Neu5Gc).

The present invention additionally includes a method for purification of antibodies specific to sialic acid groups comprising: (a) exposing an antibody containing solution to a first immobilized target that has a very low density of the sialic acid under conditions to allow antibody binding; (b) challenging the bound antibodies with a second immobilized phase comprising the first immobilized phase treated with mild sodium periodate; and collecting the antibodies that do not bind to the second immobilized phase.

It has recently been suggested that Neu5Gc may play a role in diseases, such as cancer and heart disease. Accordingly, the present invention also relates to a method for the diagnosis of disease comprising: (a) collecting a serum or tissue sample from an individual; (b) analyzing the sample for an elevated level of Neu5Gc specific antibodies in serum; and (c) correlating an increased level of antibody with the presence of disease.

Other aspects of the present invention are described throughout the specification.

The starting IgY fraction showed three times higher reactivity against bovine serum glycoproteins (which carry both Neu5Ac and Neu5Gc), than against human serum glycoproteins (which carry only Neu5Ac). The two-step affinity purification process enriched for a subset of the high affinity antibodies against Neu5Gc. Non-specific reactivity of the resulting antibody to human serum was reduced to background levels (not shown).

Figure 2:
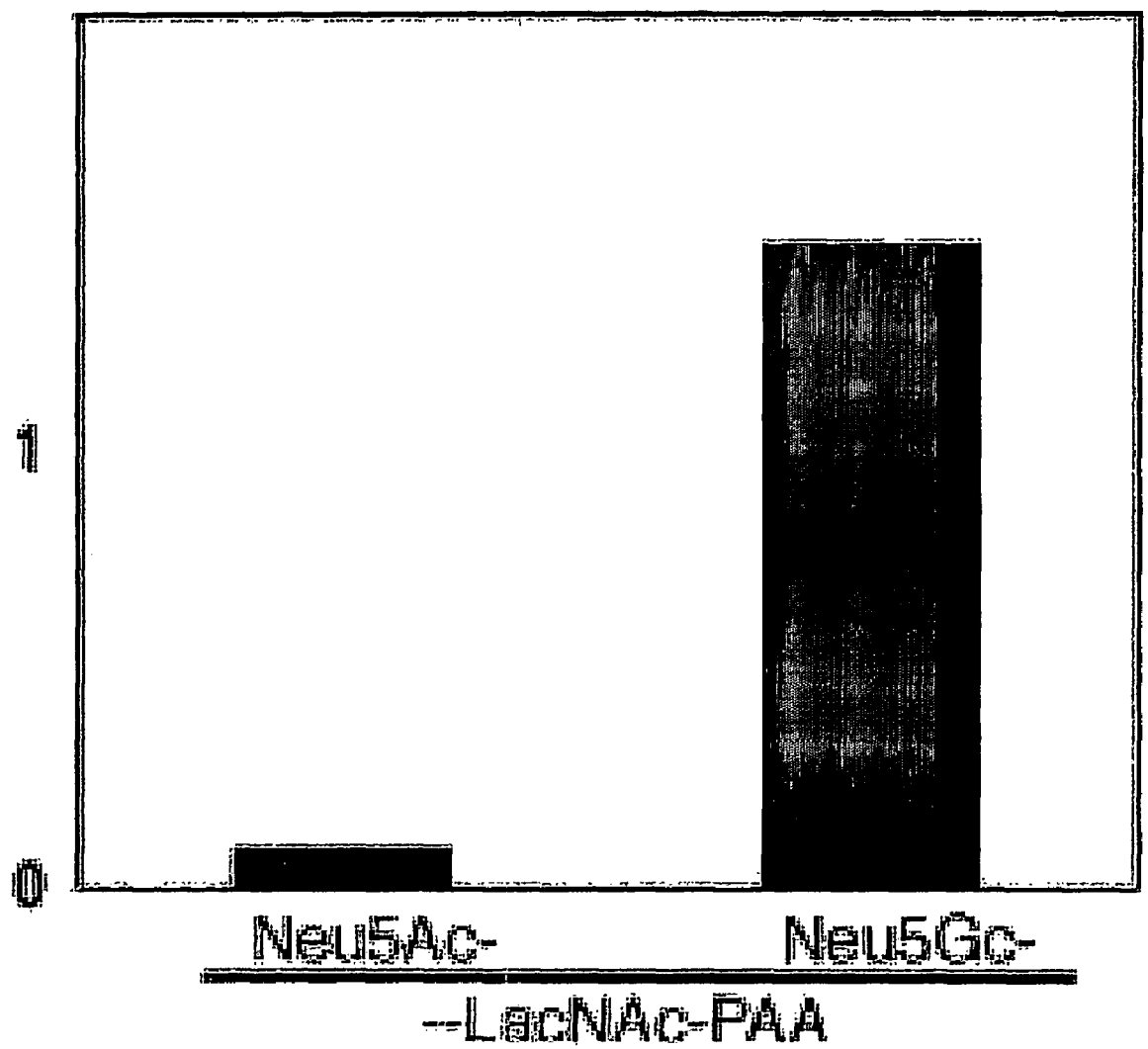

FIG. 2. Characterization of specificity of the anti-Neu5Gc antibody. ELISA against Neu5Ac-LacNAc-PAA or Neu5Gc-LacNAc-PAA. Data show the mean of three determinations.

Figure 3:
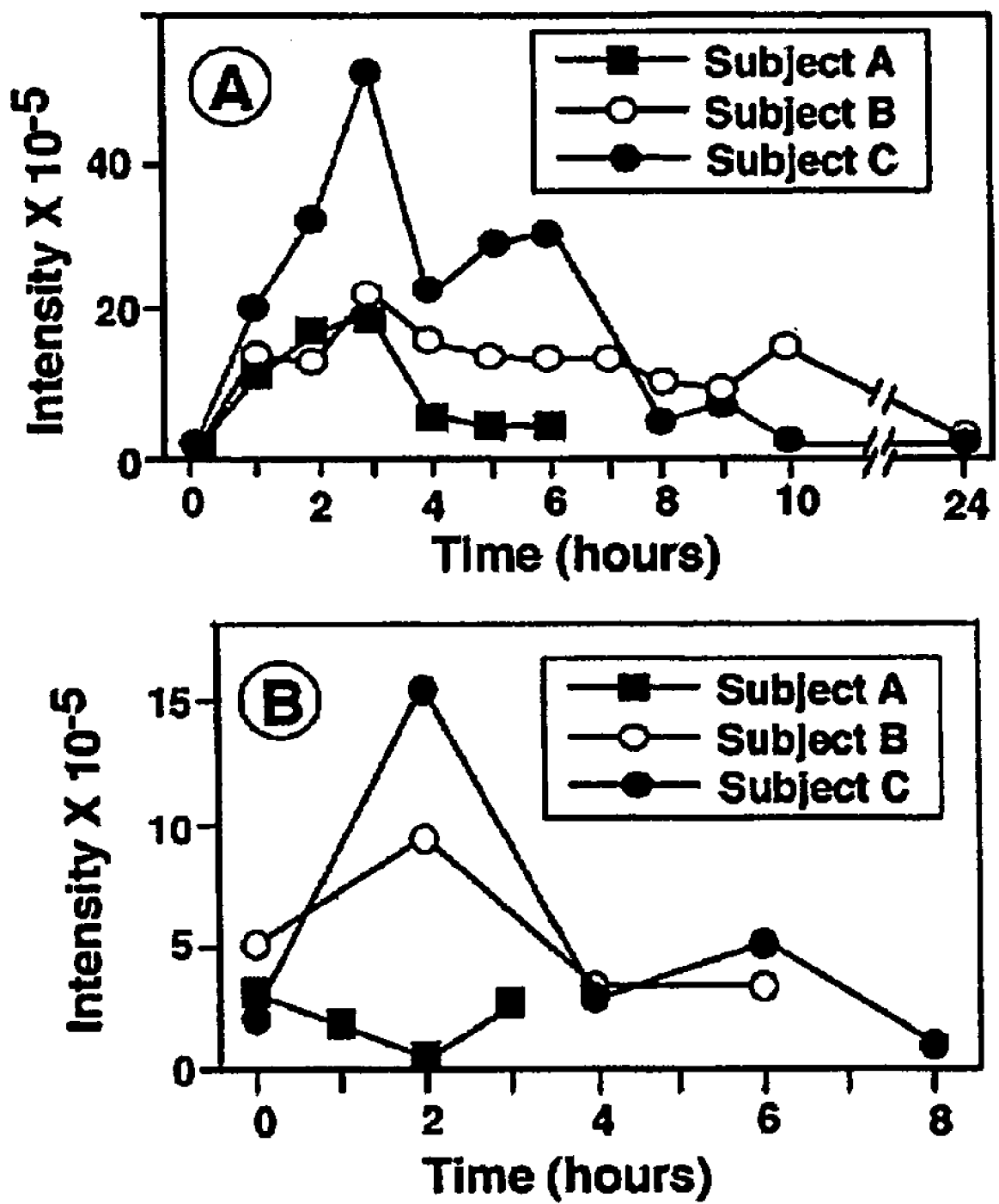

FIG. 3. Mass spectrometry detection of urinary excretion and salivary mucin incorporation of ingested Neu5Gc. Sias were purified from the urine (A) and salivary mucins (B) of the three subjects before Neu5Gc ingestion and at various subsequent time points, and analyzed by DMB-derivatization, HPLC and MS. The sum of the intensities of ions at m/z 424 and m/z 442 at each time point is plotted for each subject.

Figure 4:
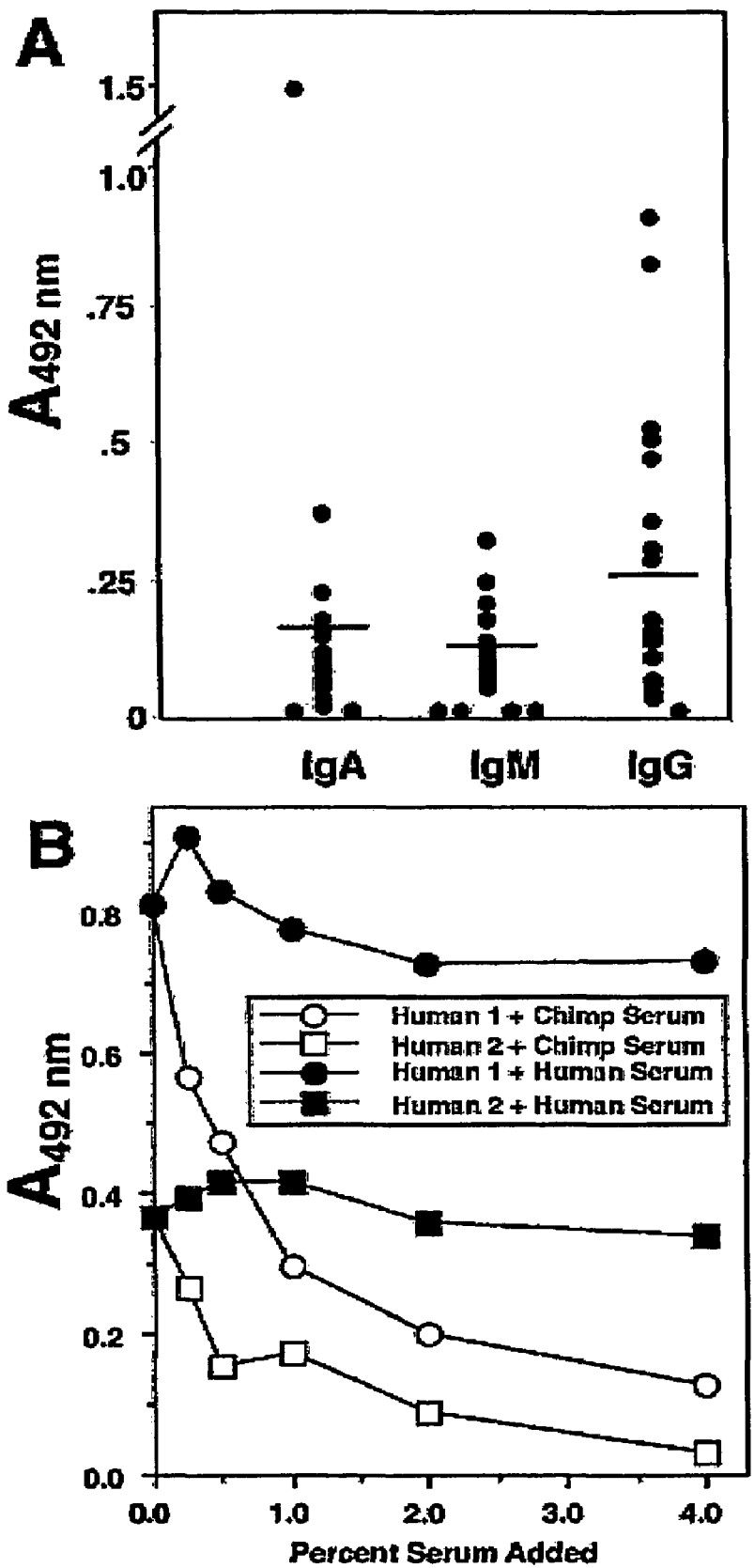

FIG. 4. ELISA detection of Anti-Neu5Gc antibodies in normal human sera and demonstration of specificity. A. Results are plotted as mean background values with PAA-Neu5Ac subtracted from the signal with PAA-Neu5Gc. The mean value for all positive sera in each sub-class is represented by the horizontal bar. B. Two of the human sera identified as medium or high positive for anti-Neu5Gc IgG antibodies to the target Neu5Gc-PAA were tested in the same ELISA assay with dilutions of chimpanzee serum added to inhibit binding. A human serum with undetectable anti-Neu5Gc antibodies was used as a control.

Figure 5:
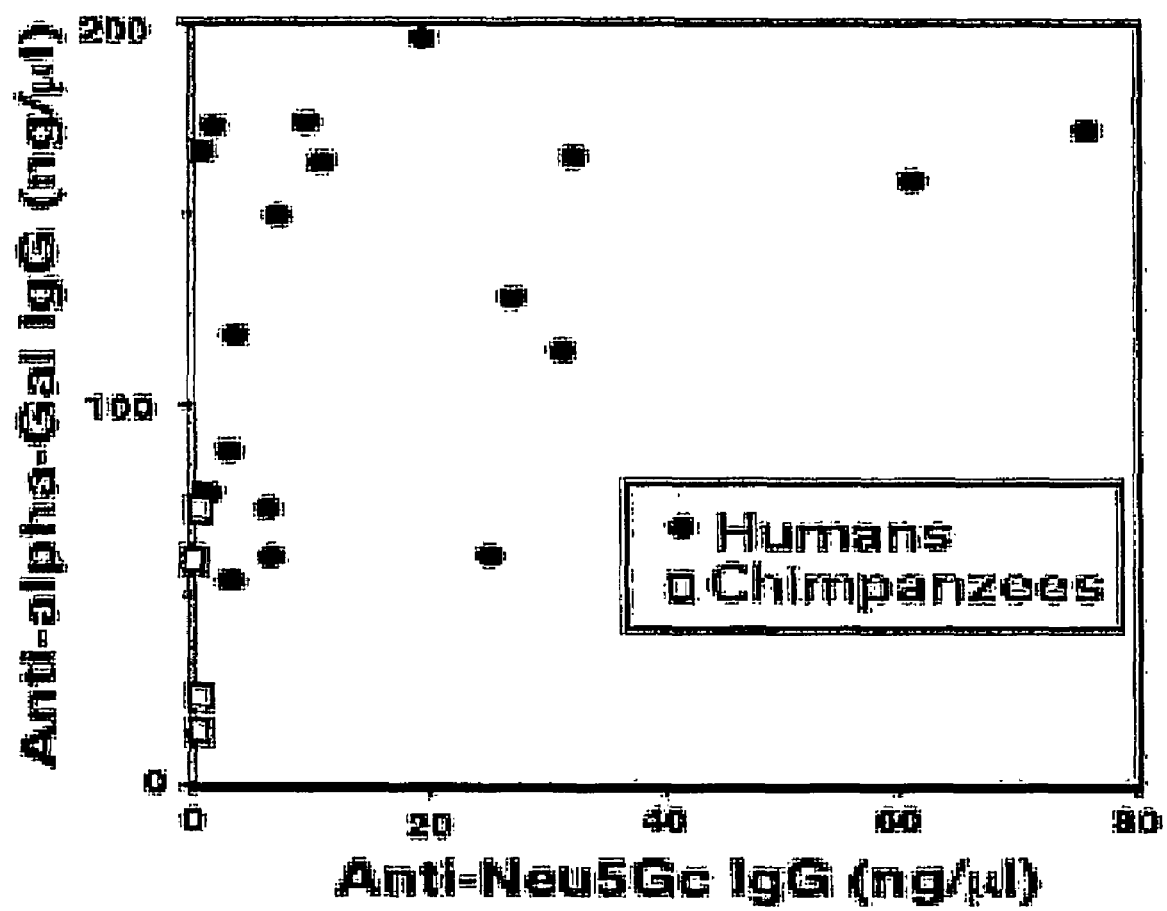

FIG. 5. Comparison of levels of anti-Neu5Gc and anti-α-Gal antibodies in normal human sera. Serum samples were collected several months later from the same individuals studied in FIG. 4A. Levels of anti-Neu5Gc antibodies were studied identically, in comparison with parallel wells coated with Galα1-3Galβ1-4GlcNAc-PAA, instead of Neu5Gc-PAA. The final readout of values was thus directly comparable between the two probes, after subtraction of the background readings with Neu5Ac-PAA. IgG levels were quantified as described.

Figure 6:
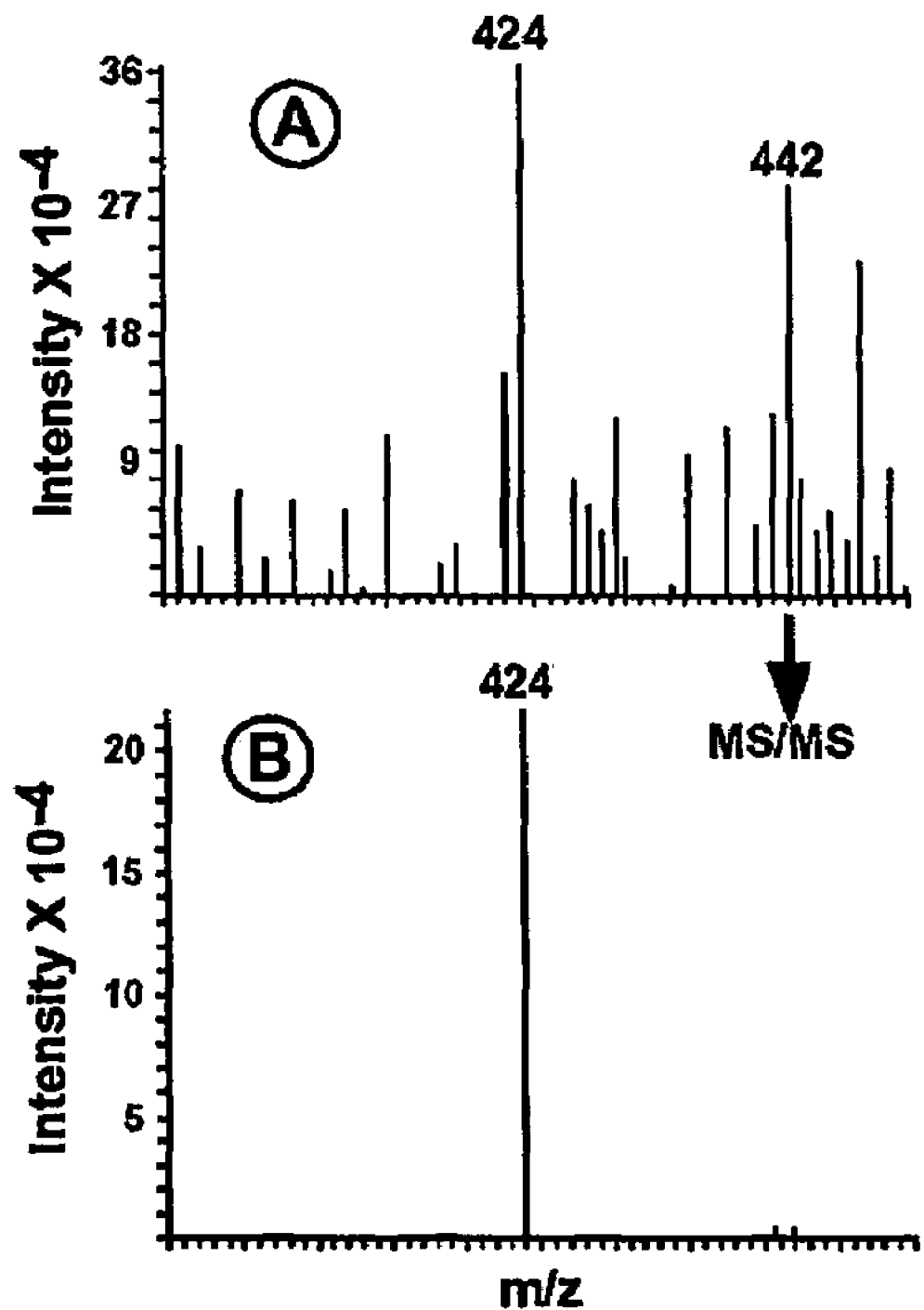

FIG. 6. Mass spectrometric detection of Neu5Gc in normal human kidney glycopeptides. Sias were released and purified from human kidney tissue, derivatized with DMB and fractionated by HPLC. (A) Mass spectrometry analysis showing ions at m/z 442 and 424, consistent with the molecular ion of DMB-derivatized Neu5Gc and its dehydrated form. (B) Selective MS/MS on the m/z 442 ion gives a fragment ion of m/z 424, confirming that the original m/z 442 ion was DMB-derivatized Neu5Gc.

Figure 7:
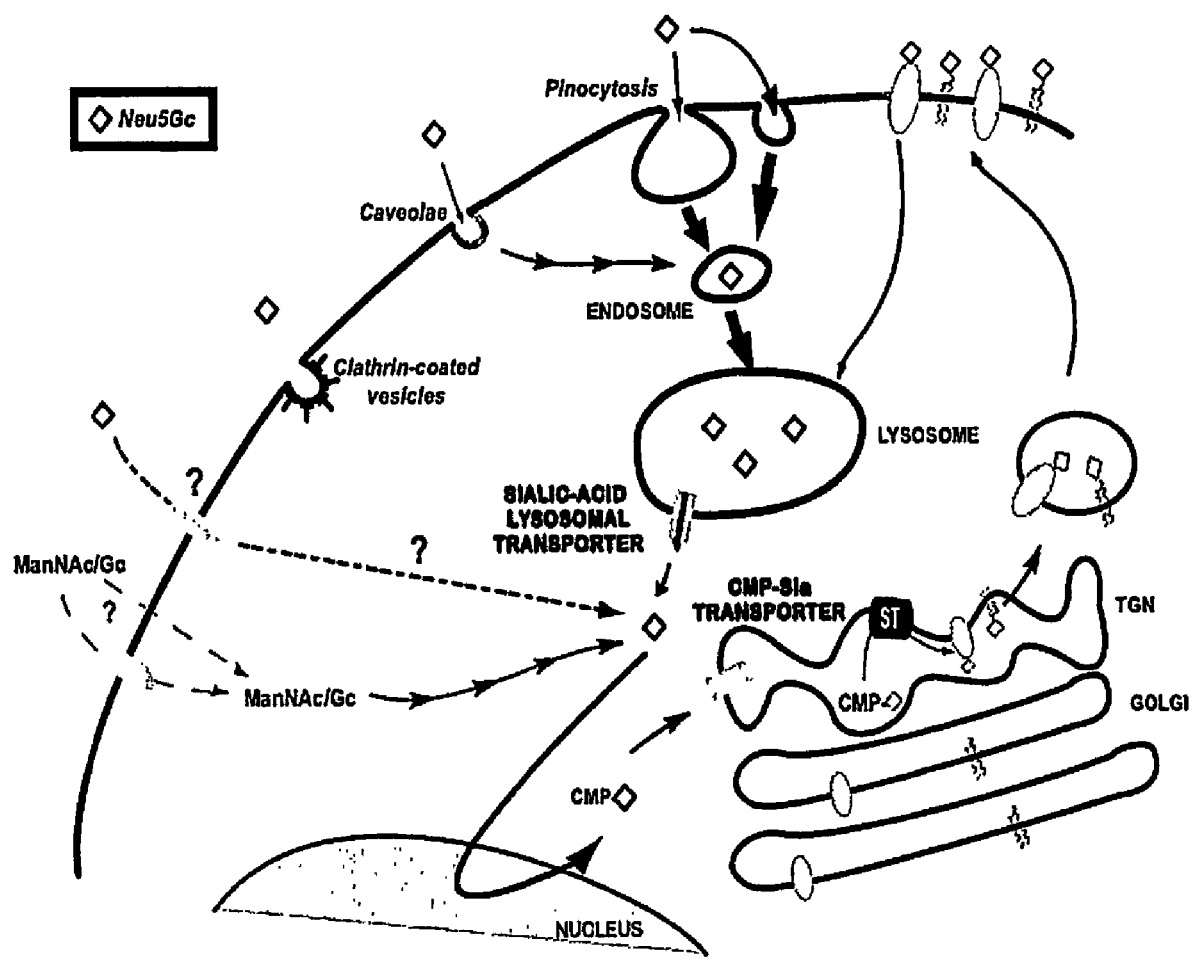

FIG. 7. Proposed pathways for uptake and incorporation of free Neu5Gc into human cells. This model is based on the literature and studies described herein. Thickness of the arrows suggests the relative importance of various pathways in delivering Neu5Gc into the cell.

DESCRIPTION OF THE INVENTION

The present application is in the field of sialic acid chemistry, metabolism and antigenicity. More particularly, the present invention relates to the detection and analysis of the non-human sialic acid, N-glycolylneuraminic Acid (Neu5Gc) in biological materials, such as food and clinical samples. For example, the analysis of Neu5Gc content in food provides useful dietary information. Additionally, the analysis of Neu5Gc and antibodies thereto in clinical specimens is useful in the prevention, prognostication and diagnosis of disease.

Preparation of Sialic Acid Specific Antibodies a. Sialic Acids

Sialic acids are 9-carbon monosaccharides that have the general structure of N-acetylneuraminic acid (Neu5Ac), which is the most common natural form of sialic acid found in humans. Sialic acids have a carboxylic acid group and a hydroxy group attached to carbon 2, which is the anomeric position of the molecule. The sialic acids differ according to the side chain attached to carbon 5 (the "side chain", as used herein), which is an N-acyl group in the Neu5Ac molecule. Many non-human naturally occurring sialic acids are known, such as Neu5Gc, which has a $CH_2OHCONH-$ side chain, instead of the $CH_3CONH-$ side chain of Neu5Ac. Another exemplary sialic acid is Ketodeoxynonulosonate (KDN). Other synthetic sialic acids have also been produced that, like Neu5Ac, can be incorporated into sialoglycoconjugates to varying degrees. These include, for example, N-propanoylneuraminic acid, N-butanoylneuraminic acid, N-pentanoylneuraminic acid, N-hexanoylneuraminic acid, N-heptanoylneuraminic acid, N-oxooctanoylneuraminic acid, N-levulinolylneuraminic acid, N-homolevulinoylneuraminic acid, N-oxohexanoylneuraminic acid, N-oxoheptanoylneuraminic acid, and N-oxooctanoylneuraminic acid. As used herein, reference to a particular sialic acid intends the naturally occurring sialic acid, the synthetic sialic acid, as well as any derivatives thereof.

b. Side Chain Removal

The sialic acid side chain can be removed by any oxidative chemical reaction, but is preferably removed with periodate.

c. Production of Antibodies

Monoclonal and polyclonal antibodies to sialic acids can be produced using known means. For example, chickens are known to be immunoresponsive to Neu5Gc, and anti-Neu5Gc IgY antibodies can be raised using the methods described in the Examples.

d. Purification of Antibodies

The production of sialic acid-specific antibodies involves a two-step procedure. In the first step, antibodies produced against sialic acids (either polyclonal or monoclonal) are contacted with a first solid phase to which the sialic acid of interest is attached. The bound antibodies are then eluted from the solid phase and thereafter challenged with a second solid phase to which the same sialic acid of interest without the side chain is attached (i.e. the "truncated form"). Antibodies that bind to the first solid phase but not the second solid phase are considered "specific" for the sialic acid of interest, since they do not bind to the truncated form of the sialic acid.

Any solid phase to which sialic acids (or sialic acid-containing molecules) can be attached is suitable for use in the method of the present invention. Such solid phases and means for attachment are well known to those of skill in the art. For example, various types of cellulose or agarose columns or ELISA plates are readily available.

Elution of bound antibodies after binding to either solid phase can be easily accomplished by washing the solid phase with the manufacturer's recommended elution buffer, such as low pH.

In addition to being useful for purifying anti-sialic acid specific antibodies, this two step approach can be used to test the specificity of monoclonal antibodies raised against sialic acids, and/or screen for their presence in clinical samples.

Uses of Anti-Sialic Acid Specific Antibodies

The antibodies prepared as described above are useful for analyzing the sialic acid content of any biological materials. The sample to be analyzed using the methods of the present invention may be from any source that is suspected of containing the sialic acid of interest. In the research laboratory, the sample may be derived from food, animal material, plant material, environmentally derived samples, etc., the sialic acid content of which is of interest to the investigator. In the clinical laboratory, the sample may similarly be derived from any food, animal material, human clinical sample, plant material, ingested substance, bodily fluid, and the like, that is associated with a clinical subject, and suspected of containing the sialic acid of interest. In particular, human serum or other bodily fluids may be investigated to detect the presence of sialic acids and their relative concentrations as an indication of a dietary condition or disease state.

Testing for Neu5Gc in Food

Neu5Gc is known to be prevalent in food sources of mammalian origin, and in particular "red meat" and dairy products. Since Neu5Gc is known to accumulate in human tissues when the subject ingests food substances containing Neu5Gc, it is important to determine the Neu5Gc content in food and to correlate intake with clinical results to assess the pathological significance of Neu5Gc content in clinical samples from human subjects.

The absolute amount of Neu5Gc in foods per serving is important, but perhaps more importantly is assessing the value of % Neu5Gc, which is the amount of Neu5Gc divided by the amount of Neu5Gc+all other sialic acids. Since Neu5Gc is predominant, the % Neu5Gc can be determined by dividing the amount of Neu5Gc by the amount of Neu5Gc+ Neu5Gc. Correlating the % Neu5Gc in foods ingested by a human subject allows for the accurate assessment of the total "body burden".

The Neu5Gc content can be expressed in terms of absolute % Neu5Gc, since Neu5Gc is generally very low in content in vegetables, fish and poultry. The Neu5Gc "load" in foods can be expressed as the total daily recommended serving, multiplied by the Neu5Gc content. For example, as shown below in Table 2, butter has 3% Neu5Gc. Butter has a total of 40 µg/g of sialic acids, which equates to 1.2 µg/g of Neu5Gc (40× 0.03=1.2). If you multiply this amount by the total recommended daily allowance of 15 grams of butter, the total Neu5Gc load of a daily serving of butter is 18 µg.

In addition, the Neu5Gc content of food on a "per serving" basis may prove to be useful labeling information for foods. As shown in Table 2, this value is easily calculated by multiplying the Neu5Gc content by the serving size. "Weight per serving" values are found on virtually every food label and are readily available from a variety of different (e.g. government) sources.

The total body uptake of Neu5Gc from a given food source may not be directly correlated to its absolute Neu5Gc content because the extent to which the food source is digested and Neu5Gc is released for adsorption might vary. The uptake of Neu5Gc from specific foods could also be used to generate a Neu5Gc index.

A "Neu5Gc index" can be used in much the same way as the glycemic index, as a numerical system of measuring how fast a given food source triggers a rise in circulating Neu5Gc. The higher the number, the greater the possibility of incorporation into body cells and tissue. A low "Neu5Gc index" food will cause a small rise, while a high index food will trigger a dramatic spike.

Testing for Neu5Gc in Clinical Specimens

The presence of Neu5Gc in human tissues may play an important role in the pathology of diseases, because of the simultaneous presence of anti-Neu5Gc antibodies circulating in the same person. Thus, Neu5Gc may play a role in heart disease, cancer, and other conditions. Also, since Neu5Gc elicits an antibody response in humans, in extreme cases, it may cause "serum sickness".

In order to assess the clinical significance of Neu5Gc content in clinical specimens, it is desirable to measure not only the absolute value of Neu5Gc, but also the % Neu5Gc as described above and in the Examples.

Detection of Anti-Neu5Gc Antibodies

As discussed above, human exposure to Neu5Gc elicits an antibody response. Since Neu5Gc is implicated in disease, the presence of high levels of Neu5Gc antibodies may also be associated with disease. As described in the Examples, Neu5Gc antibodies are detected using routine antibody screening assays. Also as described, reactivity of human sera with Neu5Ac is measured as a control, and relative reactivity is determined.

EXAMPLES

Example 1

Preparation and Characterization of Chicken Anti-Neu5Gc Antibodies

Generation of a Monospecific Chicken Polyclonal Antibody against Neu5Gc—Lipids were extracted from horse erythrocytes (Rosenberg, et al., supra), suspended in water, dialyzed against water, and fractionated on DEAE Sephadex A-25 (Schauer, et al., supra). Eluted fractions containing $G_{M3}$ (Neu5Gc) were detected by HPLC, concentrated by evaporation, dialyzed against water and taken to dryness. Chickens were immunized and boosted with 1 mg each of $G_{M3}$ (Neu5Gc) (Angata, et al., supra), except that BSA was not methylated. Other Neu5Gc-containing antigens could also be used. Egg yolks were collected, a total IgY fraction obtained by 40% ammonium sulfate precipitation, and dialyzed repeatedly against PBS, pH 7.4. Antibody titer was monitored by horse erythrocyte hemagglutination, and the pool stored at −20° C.

Columns for Affinity Chromatography—The column for pre-clearing had 81.2 mg of bovine asialofetuin (Sigma, St. Louis, Mo.) coupled to 5 ml Affi-Gel 15 beads (BioRad, Richmond, Calif.). The first affinity column contained 23.8 mg native (fully sialylated) fetuin (Sigma) coupled to 5 ml of Affi-Gel 15. A modified fetuin-column with truncated Sia side chains was prepared by treating 5 ml of an identical column with 25 ml of 2 mM sodium periodate in PBS, pH 7.4 for 30 min, rotating at 4° C. in the dark. Ethylene glycol (250 µl of 5M) was added for 5 min at 4° C. to consume excess periodate. After washing with 4×5 ml PBS, pH 7.4 and 4×5 ml 50 mM sodium acetate buffer, pH 5.5, 20 ml of 20 mM acetic hydrazide in 50 mM sodium acetate buffer, pH 5.5 was added to block reactive aldehydes generated by periodate cleavage of the Sia side chain. After 2 hrs in the dark at RT with gentle shaking, the beads were washed with 2×20 ml of PBS and resuspended in 0.01% sodium azide/PBS until use. Completeness of side chain truncation was confirmed by release of Sias using mild acid (2M acetic acid at 80° C. for 3 hrs), derivatization with 1,2-diamino-4,5-methylene-dioxybenzene (DMB) (Sigma) and HPLC analysis (Shaw, et al., supra).

Affinity Purification of Chicken anti-Neu5Gc antibody—The IgY fraction was thawed, clarified at 100,000 g for 30 min, and 1 ml of supernatant pre-cleared by passage over the asialofetuin column. The flow-through fraction was pooled with column washes of 2×5 ml PBS, pH 7.4, and passed over an affinity column containing native (sialylated) fetuin (see FIG. 4, panel A). The flow-through and washes (2×5 ml PBS, pH 7.4) were collected, and Neu5Gc-specific antibodies recovered by elution with 2×5 ml 0.1M citric acid, pH 3.0, into a vial containing 2.4 ml of 1M Tris, pH 11. Eluted fractions were monitored by ELISA against Neu5Gc-containing bovine serum (see below). The flow-through fraction was reloaded onto the same fetuin column, washed and eluted again. This procedure was repeated until there was no further binding of antibodies.

Figure 1:
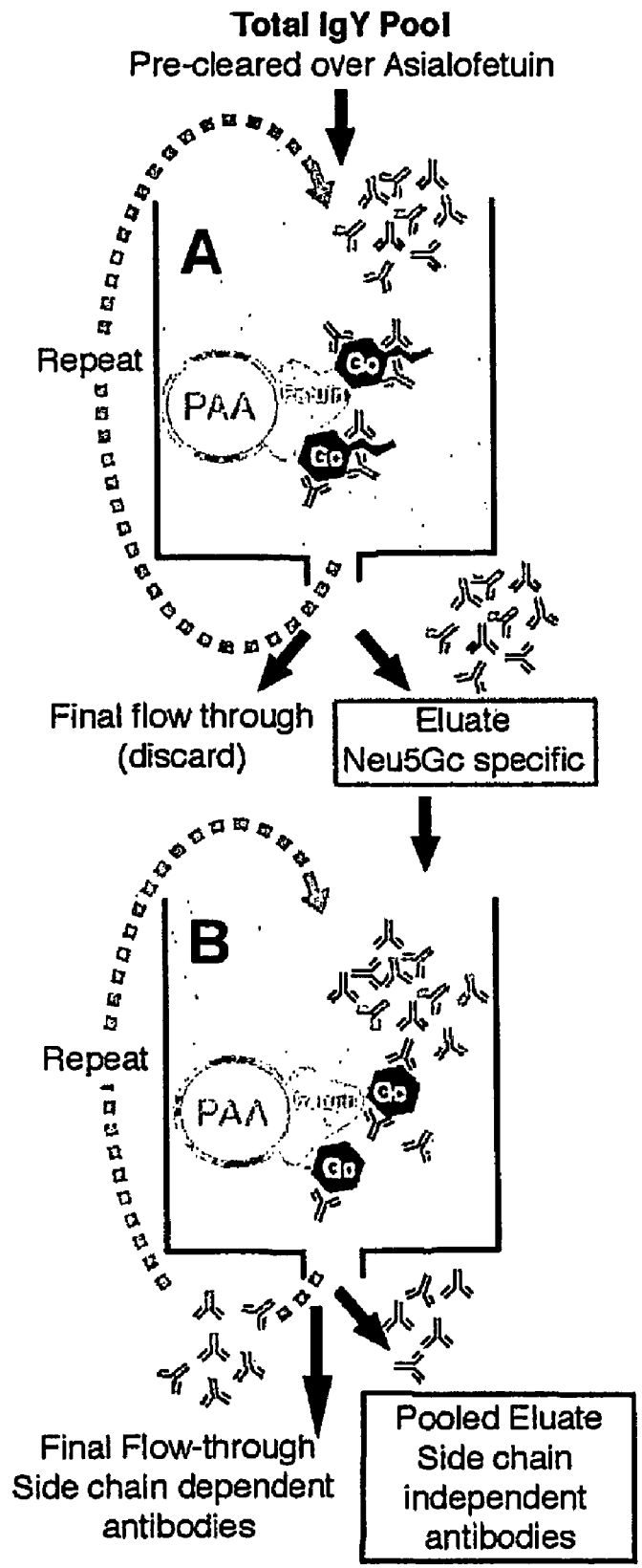
FIG. 1. Affinity-purification of a monospecific Anti-Neu5Gc antibody. The total IgY pool from eggs of chickens immunized with ganglioside $G_{M3}$(Neu5Gc) was pre-cleared over a column of immobilized bovine asialofetuin (fetuin with sialic acids removed, not shown). The flow-through fraction was passed over a column of immobilized bovine fetuin (Panel A) with a very low density of bound Neu5Gc (2.7% of total Sias). This allowed only the highest affinity antibodies to bind. These were eluted with mild acid and dialyzed against buffer. The flow-through fraction was repeatedly reapplied, until no more antibodies bound. The pooled bound fractions were then reapplied to a similar column of immobilized fetuin (Panel B), which differed only in that it had been pretreated with mild periodate oxidation to selectively truncate the side chain of Sias. Repeated rounds of this process yielded a pool of antibodies that had originally bound to the unmodified fetuin column, and continued to bind to the modified column.

Removal of side-chain dependent anti-Neu5Gc antibodies—The pooled fetuin-binding eluate fractions were concentrated to 3 ml using a Millipore Ultrafree-15 centrifugal filter device with Biomax-30K membrane (Millipore, Bedford, Mass.), and then passed over the column of fetuin with truncated Sia side chains (FIG. 1, panel B). The flow-through fraction was collected along with washes of 2×5 ml PBS, pH 7.4. The antibodies that continued to bind to this modified column were then eluted with 2×5 ml 0.1M citric acid, pH 3.0, into a vial containing 2.4 ml of 1M Tris, pH 11. The column was then re-equilibrated in PBS, and the above procedure was repeated with the flow-through fraction until there was no further decrease in reactivity to bovine serum. The combined eluates from all of the runs were concentrated to 3 ml using a Millipore Ultrafree-15 centrifugal filter device with Biomax-30K membrane.

Monitoring the Purification and Binding Specificity of the anti-Neu5Gc Antibody—Microtiter plate (Costar, Corning, N.Y.) wells were coated either with bovine serum (containing both Neu5Ac and Neu5Gc), or human serum (containing only Neu5Ac) at 115 µg protein/well, in 50 mM sodium carbonate-bicarbonate buffer, pH 9.5, at 4° C. overnight. Wells were washed with Tris buffered saline (TBS), pH7.5, and subsequently blocked with TBS+0.1% Tween (TBST) for 1 hour at RT. The wells were again washed 5× with TBS, and incubated with serial dilutions of the antibody in TBST for 2 h at RT, washed 5× again with TBS, and then incubated with a donkey anti-chicken IgY antibody conjugated with horse radish peroxidase (Jackson ImmunoResearch, West Grove, Pa.) at a 1:10,000 dilution in TBST for 1 hour at RT. After 5 washes in TBS, antibody binding was measured using 2.75 mM O-phenylene-diamine (OPD) (Sigma,) and 0.075% hydrogen peroxide in citrate phosphate buffer, pH 5.5; quenching with 40 µl of 4M sulfuric acid, and reading absorbance at 492 nm with a microplate spectrophotometer (Molecular Devices, Sunnyvale, Calif.).

Results and Discussion—Chickens are the only species other than humans known to generate an immune response to injected Neu5Gc (Kawachi, et al., supra; Fujii, Y., Higashi, H., Ikuta, K., Kato, S. and Naiki, M. (1982), Mol. Immunol. 19:87-94; Hirabayashi, Y., Suzuki, T., Suzuki, Y., Taki, T., Matsumoto, M., Higashi, H. and Kato, S. (1983), J. Biochem. (Tokyo) 94:327-330; and Asaoka, H., Nishinaka, S., Wakamiya, N., Matsuda, H. and Murata, M. (1992), Immunol. Lett. 32:91-96). Hirabayashi, et al., supra, attempted to affinity purify such antibodies using a Neu5Gc-containing glycolipid column, but did not rigorously define specificity. The method described below is a multi-step approach to affinity chromatography that optimizes the specificity and avidity of the final preparation (See FIG. 1 for details). The antibody preparation that bound to the fetuin column and then rebound to a modified fetuin column reacted with synthetic Neu5Gc-LacNAc-PAA but not with Neu5Ac-LacNAc-PAA, which differ by only a single oxygen atom (FIG. 2). It also recognized many proteins in bovine and chimpanzee sera, but not in human serum (data not shown). Note that chimpanzee proteins are ~99-100% identical to those of humans) (Goodman, M. (1999), Am. J. Hum. Genet. 64:31-39). Sialidase pretreatment abrogated reactivity (data not shown). Antibody specificity was confirmed for immunohistochemistry analyses (not shown), where chimpanzee tissue sections stained intensely and human tissues showed only a limited staining, (the latter was later shown to be specific, see below). In addition to the original immunogen (Neu5Gcα2-3Galβ1-4Glc1-1 'Ceramide), this preparation recognizes Neu5Gc in either α2-3 or α2-6 linkage to underlying Galβ1-4GlcNAc(LacNAc)-PAA (not shown). This reactivity was also blocked by chimpanzee, but not human serum (not shown). Thus, this polyclonal preparation contains antibodies recognizing Neu5Gc on both glycoproteins and glycolipids, regardless of the linkage (α2-3 or α2-6), and regardless of the underlying sugar chain. Binding to synthetic PAA-based probes confirms that the nature of the protein or the lipid tail of glycolipids are not important binding determinants.

Example 2

Studies Using Chicken Anti-Neu5Gc Antibody

Immunohistochemistry using the Chicken Anti-Neu5Gc Antibody—Human tissues were collected from autopsies or unused pathological material, frozen in OCT compound (VWR International) and archived at −70° C. Frozen chimpanzee tissue was provided by the Yerkes Primate Center, Atlanta, Ga. Frozen tissue sections were air-dried for 30 min., fixed in 10% buffered formalin for 30 min, endogenous peroxidase activity quenched and non-specific binding sites blocked with 5% (Neu5Gc free) human serum in PBS for 30 min. Sections were then incubated with the anti-Neu5Gc antibody in 5% human serum/PBS at a 1:200 dilution at room temperature (RT) for 2 h. After washing, HRP-conjugated donkey anti-chicken IgY antibody in 5% human serum/PBS at a 1:100 dilution was applied for 1 hr. Control sections were incubated with secondary reagent only. Specific binding was detected using the Nova Red substrate kit (Vector Laboratories, Burlingame, Calif.), followed by hematoxylin counterstaining.

The staining pattern is summarized in Table I below:

TABLE 1

Reactivity of normal human tissue sections with the anti-Neu5Gc antibody.

| Tissue | Staining Pattern* |
|---|---|
| Lung | Endothelium of blood vessels: Luminal edges of bronchiolar epithelial cells and associated secretions. |
| Skin | Endothelium of blood vessels: Luminal edges of epithelial cells of eccrine glands and associated ducts. |
| Colon | Endothelium of blood vessels: Luminal edges of colonic epithelial cells and associated secretions. |
| Prostate | Endothelium of blood vessels: Cytoplasmic staining of glandular epithelial cells (faint). |

TABLE 1-continued

Reactivity of normal human tissue sections
with the anti-Neu5Gc antibody.

| Tissue | Staining Pattern* |
|---|---|
| Uterus | Epithelial cells of Endometrial glands (non-secretory phase studied). |
| Kidney | Edges of collecting duct epithelium and associated secretions: No glomerular staining. |
| Spleen | Endothelium of blood vessels: Periarteriolar lymphoid sheath lymphocytes. |
| Pancreas | Endothelium of blood vessels: Epithelial cells of acini (faint). |
| Testis | Endothelium of blood vessels: Basal cell layer (spermatogonia) of the seminiferous tubules (faint). |
| Liver | Endothelium of blood vessels: Luminal edges of some bile duct epithelial cells. |
| Fetal Stomach | Endothelium of blood vessels: Luminal edges of epithelial cells of the villi and associated secretions. |
| Placenta | Endothelium. |
| Breast Carcinoma | Majority of carcinoma cells and some blood vessels. |

Staining with the antibody showed cell-type specific reactivity in adult human tissues. Breast carcinomas showed reactivity in the majority of tumor cells and some related blood vessels. Reactivity was also confirmed in 3/5 colon, 3/3 lung and 2/4 ovarian carcinomas and in 1/2 melanomas (unpublished). In the fetus, staining was prominent in epithelial cells and secretions, as well as in the placental villus blood vessels. The overall pattern of staining in 12 normal human tissues can be summarized as prominent in secretory epithelia and associated secretions, and present in many blood vessels. Secondary antibody alone gave no staining (not shown). The ability to specifically inhibit staining by chimpanzee serum or by porcine mucin varied with individual human tissues (not shown). However, in comparison to wild-type mice, no clear staining was seen in tissues from CAMH null mice that are expected to be Neu5Gc deficient (unpublished collaboration with Takematsu et al.) Thus, the variable inhibition by chimpanzee serum or porcine mucin in different human tissues may reflect expression of different types of Neu5Gc-containing epitopes. Of course, it could not be ruled out that a novel human-specific epitope that is not Neu5Gc was cross-reacting with this extensively characterized antibody, so MS analysis was performed.

Detection of Neu5Gc by HPLC Analysis and Mass Spectrometry (MS)—Human autopsy tissues (0.5 g) were subjected to sequential organic extractions and glycopeptides preparation (Muchmore, et al., supra). Sias in glycopeptides and lipid extracts were released by acid and purified by ion exchange chromatography (Varki, A. and Diaz, S. (1984), *Anal. Biochem.* 137:236-247), derivatized with 1,2-diamino-4,5-methylene dioxybenzene (DMB) and analyzed by HPLC (DMB-HPLC) and MS (Chou, et al., supra, and Klein, A., Diaz, S., Ferreira, I., Lamblin, G., Roussel, P. and Manzi, A. E. (1997), *Glycobiology* 7:421-432).

A Neu5Gc standard gave signals at m/z 442 and 424, consistent with molecular ions of DMB-derivatized Neu5Gc and its dehydrated form (not shown). As expected, selective secondary MS on the m/z 442 ion peak gave the m/z 424 dehydrated form (not shown). MS on putative-DMB-derivatized Neu5Gc from human kidney also gave ion peaks at m/z 442 and 424 (FIG. 6A). Selective secondary MS of the m/z 442 ion gave a single ion peak at m/z 424, confirming the presence of Neu5Gc (FIG. 6B). Analysis of glycopeptides and some glycolipid fractions from human heart, liver and spleen tissues gave similar spectra. MS done in this manner is not truly quantitative. However, there were previously reported small HPLC peaks from normal adult human tissues eluting in the position expected for Neu5Gc (Muchmore, et al., supra). These peaks (now confirmed to be Neu5Gc) represented <1% of total Sias in liver, skin and kidney; ~1% in spleen and testes; and, ~2% in the heart.

Purification of Neu5Gc from porcine submaxillary mucin—Frozen porcine submaxillary glands (Pel-Freeze Biologicals, Rogers, Ariz.), were minced, homogenized in water, and total mucins precipitated from the water-soluble supernatant by slow acidification to 100 mM acetic acid in the cold for a few hours. The precipitate was resuspended in water, the pH neutralized, and dialyzed against water. Sia content was determined by DMB-HPLC analysis. Sias were released with mild acid, collected by dialysis (1000 molecular-weight-cut-off), de-O-acetylated and purified on ion exchange columns (Gottschalk, et al., supra). Remaining contaminants were removed with a C18 cartridge. The yield was 563 mg of Sia (95% Neu5Gc, 5% Neu5Ac) from 28.2 g of mucin.

Example 3

Uptake of Neu5Gc by Cultured Human Cells

Feeding of Human Epithelial Cells with Neu5Gc—Caco-2 cells (human epithelial cells isolated from a primary colon carcinoma, ATCC, Manassas, Va.), were propagated in α-MEM (Gibco, Invitrogen Corporation, San Diego, Calif.) supplemented with 20% heat inactivated Fetal Calf Serum, at 37° C., 5% $CO_2$. Prior to feeding, the cells were split and cultured for 4 days in α-MEM supplemented with 20% heat inactivated premium human serum type AB (Irvine scientific, Santa Ana, Calif.). Cells were then cultured in the presence of various concentrations of free Neu5Gc (0, 0.3, 1 and 3 mM, respectively) for 3 days at 37° C. Cells were then washed with cold PBS, scraped into 20 mM sodium phosphate pH 7.5 and sonicated. The protein extract was quantified and analyzed by Western blot using the anti-Neu5Gc antibody.

Western Blot Analysis—Serum proteins or total proteins extracted from Neu5Gc-fed or non-fed Caco-2 cells were either treated or sham treated with 10 mU *Arthrobacter ureafaciens* sialidase (EY Labs, San Mateo, Calif.) in 100 mM sodium acetate, pH 5.5 at 37° C. for 3 h. After SDS-PAGE electrophoresis, the separated proteins were transferred to nitrocellulose membrane, and binding of the anti-Neu5Gc antibody (1:10,000 in Tris-buffered saline with 0.1% Tween 20 (TBST)) was detected using a secondary HRP-conjugated donkey anti-chicken IgY antibody (1:30,000 in TBST) and Supersignal West Pico (Pierce, Rockford, Ill.).

Although human cells cultured in fetal calf serum express cell surface Neu5Gc in small amounts (Muchmore, et al., supra, and Oetke, et al., supra), this could represent either metabolic incorporation or non-specific absorption. Human epithelial cells were cultured in human serum until no traces of Neu5Gc derived from fetal calf serum could be detected by HPLC (typically ~4 days). Culture was then continued for 3 days in the absence or presence of varying amounts of free Neu5Gc. HPLC analysis showed increasing incorporation of Neu5Gc into the cells over time, with the highest level reaching 85% of total Sia, after incubation in 3 mM Neu5Gc for 3 days (data not shown). Metabolic incorporation of Neu5Gc into glycoproteins was confirmed by Western blotting using the anti-Neu5Gc antibody (data not shown). Staining was only seen when Neu5Gc was present in the medium, and reactivity was eliminated by sialidase treatment (further confirming the specificity of the antibody). These data suggested that the small amounts of Neu5Gc in normal human tissues could originate from dietary sources.

Example 4

Human Ingestion Studies

Human Neu5Gc Ingestion Study—Human subjects were enlisted in the study, and were told to avoid animal foods for 2 days, all medications for 1 day, use a lanolin-free (Neu5Gc-free) shampoo for 2 days, and ingest only fruit juice on the morning of study. Subjects then drank 150 mg of porcine submaxillary mucin Sias (see above) dissolved in 100 ml water. For the next 6 h they drank a 1:1 mixture of fruit juice and soymilk (Sia free) at ~2 ml/Kg/hr. Serum, urine and saliva samples were obtained at multiple time points. Human saliva was collected by chewing parafilm, after washing the mouth out well with water. Urine volume and pH were recorded prior to centrifugation at 1000 g for 10 min, and collection of the supernatant. All samples were stored frozen at −20° C. Head hairs (~20) and/or facial hair trimmings (from men) were collected prior to, and on several days after Neu5Gc ingestion.

Purification and analysis of Sialic Acids and N-acylmannosamines from Human Samples—Human salivary mucin was precipitated by adjusting to pH 3 with 100 mM acetic acid, stirring at 4° C. overnight, collected at 14,000 g for 10 min, and washed twice with 1 ml of ice-cold PBS. Human hair clippings were washed in 100 mM ice-cold acetic acid for two h and crushed in a clean ceramic mortar. Bound Sias from saliva, hair or serum were released with mild acid as above, filtered through Microcon 10 filters (Millipore, Bedford, Mass.), dried down, reconstituted in water and analyzed for Sia content by DMB-HPLC.

Five ml urine aliquots were diluted 5-fold and loaded onto 10 ml columns of AG50W-X2 resin ($H^+$ form, BioRad, Richmond, Calif.) equilibrated in water. The run-through and washes (2×10 ml of water) were pooled and loaded onto 10 ml columns of AG1X8 resin (Formate form, BioRad) equilibrated in water. The combined run-through and washes (2×10 ml of water) were lyophilized. After washing with 5 volumes of 10 mM formic acid, free Sias were eluted with 5 volumes of 1M formic acid, diluted two-fold with water, and lyophilized.

The neutral fraction from urine was dissolved in water and reduced peracetylated volatile derivatives of free sugars prepared (Bjorndal, H., Lindberg, B., Pilotti, A. and Svensson, S. (1967), *Carbohydr. Res.* 5: 433-440). Samples were dissolved in 10 ul of acetone, and gas-liquid chromatography for N-acylmannosamines performed on 1 ul aliquots (Bjorndal, et al., supra). Eluting ions were detected and fragmented using a HP5971 Mass Selective Detector (Hewlett-Packard, Palo Alto, Calif.).

Free Sias were purified from urine samples, and analyzed for Neu5Gc content by DMB-HPLC. Since overlapping fluorescent peaks prevented definitive identification and quantification, HPLC fractions eluting at the time expected for DMB-Neu5Gc were collected and subjected to MS, confirming an increase in ion peaks at m/z 424 and m/z 442. The sum of ion intensities of m/z 424 and m/z 442 at each time point provided an estimate of Neu5Gc quantity. Ingested Neu5Gc was rapidly absorbed and excreted into the urine (FIG. 3A). About 3-6% of the ingested dose was excreted within 4-6 h, with the peak excretion rate at 2-3 h and a return to baseline levels within 24 h. Notably, small amounts of Neu5Gc were also present at baseline.

Sias could be converted into their corresponding acylmannosamines by sialate:pyruvate-lyases (Schauer, R., Sommer, U., Krüger, D., Van, U. H. and Traving, C. (1999), *Biosci. Rep.* 19:373-383), derived from either intestinal cells or gut microbes. Such molecules could then enter cells and be reconverted back to the original Sias (Kayser, H., Zeitler, R., Kannicht, C., Grunow, D., Nuck, R. and Reutter, W. (1992), *J. Biol. Chem.* 267:16934-16938). To ascertain potential conversion of the ingested Neu5Gc into N-glycolylmannosamine (ManNGc), presence of this neutral sugar in the urine was investigated. Small amounts of ManNGc were present at baseline in one subject (not shown). There was no obvious increase over time in any subject (not shown), indicating that the remaining ingested Neu5Gc was not absorbed and excreted as ManNGc. Thus, much of the uptake is apparently occurring as free Neu5Gc.

The possibility that ingested Neu5Gc was incorporated into newly synthesized glycoproteins was also investigated. Mucins from all baseline saliva samples showed very small amounts of Neu5Gc detectable by MS. An increase 2 days after ingestion occurred in 2 of 3 subjects, with a decline to baseline levels by 4 days (FIG. 3B). While Neu5Gc was not detected in serum samples at any time points, small amounts were found in facial hair clippings at baseline for two subjects, with increases after ingestion. Overall the data show uptake and excretion of intact Neu5Gc, and low-level metabolic incorporation into newly synthesized glycoconjugates. Although there were no immediate reactions to Neu5Gc ingestion, this does not rule out long-term consequences.

Example 5

Anti-Sia Antibodies in Human Sera

Detection of Anti-Neu5Gc and anti-α-Gal specific antibodies in human sera—Microtiter (Costar, Corning, N.Y.) plate wells were coated with Neu5Ac-polyacrylamide(PAA), Neu5Gc-PAA, or Galα1-3GalBeta1-4GlcNAc-PAA (Glycotech, Rockville, Md.) at a concentration of 500 ng/well, in 50 mM sodium carbonate-bicarbonate buffer pH 9.5, at 4° C. overnight. After washing with TBS, pH 7.5 and blocking with TBST for 2 h at RT, triplicate wells were incubated with 1:50 dilutions of serum in TBST at RT for 4 h. Wells were washed 5 times with TBS, and incubated with HRP-conjugated mouse anti-human IgA (Calbiochem, San Diego, Calif.), anti-human IgG (Jackson ImmunoResearch, West Grove, Pa.) or anti-human IgM (KPL, Gaithersburg, Md.) each diluted in TBST at 1:20,000, at RT for 1.5 hour. The IgG anti-Neu5Gc and anti-α-Gal antibodies were quantitated using a standard curve of normal human IgG coated to the wells under the same general conditions.

Anti-Neu5Gc antibodies of the IgA, IgM and IgG classes were detected in the sera of all three subjects who ingested Neu5Gc at baseline, but no increases occurred after Neu5Gc ingestion (not shown). Studies of additional normal adults showed that 16/18, 14/18 and 17/18 sera were positive for IgA, IgM and IgG antibodies, respectively (FIG. 4A). Specificity was confirmed by showing that anti-Neu5Gc reactivity was blocked by chimpanzee serum in a concentration-dependent manner, but not by equivalent amounts of a Neu5Gc antibody-negative human serum (FIG. 4B). The chimpanzee serum used for inhibition was also negative for anti-Neu5Gc antibodies (FIG. 5). Further confirmation came from >70% inhibition of reactivity by free Neu5Gc but not by Neu5Ac (each at 2 mM, not shown).

Some human sera required up to 3-4% chimpanzee serum to obtain complete blockade (FIG. 4B). Since chimpanzee serum glycoproteins carry ~0.1 nmol of Neu5Gc per ul, the anti-Neu5Gc antibodies must be present at relatively high concentrations in such human sera. Indeed, these antibodies represented up to 0.25% of the total circulating IgG in some subjects (FIG. 5). This falls into the range of the well-known xeno-reactive antibodies against the non-human α-Gal epitope (Galili, U. *Immunol Today* 14:480-482; and Joziasse, D. H. and Oriol, R. (1999), *Biochem. Biophys. Acta Mol. Basis Dis.* 1455:403-418). We also compared levels of IgG anti-Neu5Gc and anti-α-Gal antibodies. As expected from prior literature, all the human sera contained easily detectable anti-α-Gal antibodies. Anti-Neu5Gc levels were highly variable, and there was no direct correlation between the two antibody levels in any given individual. On the other hand, the relative levels of anti-Neu5Gc antibodies between individuals were reproducible on repeat sampling. Four chimpanzee sera showed no anti-Neu5Gc antibodies, but clear evidence of anti-α-Gal antibodies (FIG. 5).

Example 6

Sialic Acids in Food Samples

Purification and Analysis of Sialic Acids from Food Samples—One gram portions of samples were homogenized in 2M acetic acid, and total Sias released at 80° C. for 3 h. After clarification at 50,000 g, the supernatant was filtered through a Microcon 10 unit, dried down, reconstituted in water, de-O-acetylated with 0.1M NaOH for 30 min at 37° C., and neutralized with HCl. Aliquots were derivatized with DMB and Neu5Gc content analyzed by HPLC and MS as described above.

The results are shown below in Table 2:

As shown above, Neu5Gc is enriched in food sources of mammalian origin. Sias have never been detected in plants, and are found in large amounts primarily in vertebrates and in a few "higher" invertebrates (Rosenberg, et al., supra; Schauer, et al., supra; and Warren, L. (1963), *Comp. Biochem. Physiol.* 10:153-1712). While several pathogenic microbes can express Neu5Ac, none have been reported to express Neu5Gc.

As shown above in Table 2, the highest amount was found in lamb, pork and beef (so-called "red meat"). In contrast, levels were very low or undetectable in poultry and in fish. Hen's eggs contain primarily Neu5Ac (Juneja, L. R., Koketsu, M., Nishimoto, K., Kim, M., Yamamoto, T. and Itoh, T. (1991), *Carbohydr. Res.* 214:179-186). Intermediate amounts were found in bovine milk and milk products, with higher levels in goat and sheep milk products. As summarized in Table 2, USDA recommended dietary intake would result in substantial intake of Neu5Gc from red meats, and moderate amounts from dairy products. This survey is a limited sampling of human food. A much broader survey using the same techniques is needed to fully establish the possible sources of Neu5Gc in human diet.

Example 7

Neu5Gc Metabolism

Using the methods described herein, Neu5Gc is detectable in fetal small intestine and placenta, and its presence in 9/9 breast 3/5 colon, 3/3 lung and 2/4 ovarian carcinomas and in 1/2 melanomas has been found. Surprisingly, secretory epithelia and endothelium within certain normal adult human tissues (lung, skin, colon, prostate, uterus, testis) also showed

TABLE 2

Preliminary survey of total sialic acid and Neu5Gc content of common food items

| Food item | % Neu5Gc* | Total Sia,*, µg/g | Neu5Gc content, µg/g | Serving size,† g | Servings per day† | Total wt if eaten daily, g/day | Neu5Gc intake if eaten daily,‡ µg | Neu5Gc per Serving, µg |
|---|---|---|---|---|---|---|---|---|
| Cod | <0.1 | 40 | <0.04 | 90 | 3 | 270 | <11 | — |
| Salmon | <0.1-3.5 | 49 | 1.47 | 90 | 3 | 270 | <11-397 | 132 |
| Tuna | <0.1 | 32 | <0.032 | 90 | 3 | 270 | <9 | — |
| Chicken | <0.1 | 76 | <0.076 | 90 | 3 | 270 | <21 | — |
| Turkey | <0.1-0.6 | 46 | <0.046 | 90 | 3 | 270 | <12-75 | — |
| Duck | <0.1 | 20 | <0.02 | 90 | 3 | 270 | <5 | — |
| Cow milk (2%) | 3 | 258 | 7.74 | 237 | 2 | 474 | 3,668 | 1,834 |
| Cow milk (raw) | 3 | 262 | 7.86 | 237 | 2 | 474 | 3,726 | 1,863 |
| Butter | 3 | 40 | 1.2 | 5 | 3 | 15 | 18 | 6 |
| Cow cheese | 4 | 160 | 6.4 | 50 | 3 | 150 | 960 | 320 |
| Goat cheese | 42 | 95 | 39.9 | 44 | 3 | 132 | 5,267 | 1,756 |
| Lamb | 18 | 101 | 18.2 | 90 | 3 | 270 | 4,914 | 1,638 |
| Pork | 19 | 134 | 25.5 | 90 | 3 | 270 | 6,885 | 2,295 |
| Beef§ | 31-43 | 70 | 30.1 | 90 | 3 | 270 | 5,859-8,127 | 2,709 |

*Total Sia content and percent of Neu5Gc in each food sample was quantified as described herein. Range of values obtained are shown for food items that were studied more than once. Oral intake calculations include the highest values in such cases.
†Recommended daily servings and serving sizes of each item are based on guidelines set by the U.S. Department of Agriculture [U.S. Department of Agriculture (2000) Nutrition and Your Health: Dietary Guidelines for Americans (U.S. Department of Agriculture, Washington, DC), Home Garden Bulletin 323, 5th Ed.].
‡Oral intake calculation only. Actual bioavailability is unknown.
§Lean beef and beef fat portions had similar Neu5Gc contents (data not shown).

reactivity with anti-Neu5Gc antibodies. The presence of Neu5Gc in such samples was confirmed by HPLC and MS. (Tangvoranuntakul, P., Gagneux, P., Diaz, S., Bardor, M., Varki, N., Varki, A. & Muchmore, E. (2003). *Proc Natl Acad Sci USA* 100:12045-12050.)

Cultured Human cells can also take up and incorporate free Neu5Gc or Neu5Gc from fetal calf serum glycoproteins. The hydroxylase activity responsible for generating Neu5Gc is encoded by the single copy CAMH gene, which has been highly conserved from Sea Urchins to Primates. The only known homologs of this gene are distantly related hydroxylases in bacteria and plants (Schmidt, C. L. and Shaw, L. A (2001). *J. Bioenerg. Biomembr.* 33:9-26. An alternative pathway for Neu5Gc synthesis involving Glycolyl-CoA as a donor has been postulated only in principle, but never proven (Vamecq, J. & Poupaert, J. H. (1990). *Biochem. Cell Biol.* 68:846-851; and Vamecq, J., Mestdagh, N., Henichart, J.-P. and Poupaert, J. (1992). *J Biochem (Tokyo)* 111:579-583.

It is therefore reasoned that the Neu5Gc in normal humans originates from exogenous sources. Indeed, human cells fed with free Neu5Gc incorporated it into endogenous glycoproteins, achieving levels of >50%, comparable to those found in ape cells. Likewise, human cells cultured in FCS incorporated Neu5Gc from the serum glycoproteins into the native glycoconjugates of the cells (Muchmore, E. A., Diaz, S. and Varki, A. (1998). *Am J Phys Anthropol* 107:187-198; and Tangvoranuntakul, et al., supra.

It was also found that the uptake of both free Neu5Gc and Neu5Gc-containing proteins involves micro- and macro-pinocytosis, delivery to the lysosome, and export into the cytosol by the lysosomal Sia transporter (in the case of serum protein-bound Neu5Gc, release by a lysosomal sialidase is required before transport into the cytosol) (FIG. 7). Once free Neu5Gc has reached the cytosol, it is available for activation to CMP-Neu5Gc and eventual transfer to glycoproteins, in a manner similar to endogenously synthesized Neu5Gc. Since Neu5Gc was eliminated during human evolution only ~3 million years ago, it is not surprising that the enzymes and transporters involved in activation, transport and transfer of Sias do not see it as "foreign". (Chou, H. H., et al., supra.)

It is also suspected that the lysosomal sialic acid transporter is critically involved in the uptake of Neu5Gc. To study transport, normal and lysosomal Sia transporter mutant human fibroblasts (GM 08496 and GM 05520) were fed for 3 days with 3 mM Neu5Gc, ManNGc or Neu5Ac. The cells were then harvested and fractionated and the Sia content in the different fractions analysed by DMB derivatization followed by HPLC. The % of Neu5Gc incorporation was reduced from 37% in normal fibroblasts to 5% in the mutant cells. As a control, the incorporation of ManNGc into Neu5Gc was also studied, which presumably occurs via passive diffusion through the plasma membrane, and does not require the lysosomal transporter. Indeed, it was found that there was essentially no difference between normal (19% Neu5Gc) versus mutant fibroblasts (18% Neu5Gc) following incubation with ManNGc. To further confirm that there was a difference in incorporation, a Western blot analysis of proteins extracted from the membrane of wild-type and GM 05520 mutant human fibroblasts using an anti-Neu5Gc antibody, with or without prior Neu5Gc or ManNGc feeding. This confirmed that the mutant fibroblasts could not incorporate Neu5Gc into glycoproteins, but could in fact convert it from ManNGc. Taken together, the data confirms the hypothesis that the lysosomal sialic acid transporter plays a crucial role in delivering free sialic acids that enter the cell via endocytosis to the cytosol for activation and incorporation as depicted in FIG. 7.

Example 8

Neu5Gc Antibody-Mediated Cell Destruction

Naturally occurring human antibodies (Nabs) against Neu5Gc (anti-Neu5Gc) can cause complement deposition and/or cell death of human cells loaded with Neu5Gc. To explore the possibility that the human anti-Neu5Gc Nabs can cause inflammation and/or cell killing, human cells were cultured in human serum, with or without free Neu5Gc in the medium. It has been found that upon exposure to human sera known to contain anti-Neu5Gc NAbs, the Neu5Gc-loaded cells showed reduced viability, deposition of complement (C3b) and cell killing (data not shown). There was also a correlation of extent of cytotoxicity with the relative amounts of NAbs. Cytotoxicity could be blocked by small amounts of chimpanzee serum, which is rich in Neu5Gc, but is otherwise >99% identical to human serum, which does not block this killing (data not shown). Accordingly, it is likely that anti-Neu5Gc Nabs antibodies may have an undesirable affect on cells in vivo.

The examples set forth above are provided to give those of ordinary skill in the art with a complete disclosure and description of how to make and use the preferred embodiments of the invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A method of detecting an amount of anti-Neu5Gc specific antibodies in a fluid sample comprising:
    (a) determining the amount of anti-Neu5Ac antibodies present in the fluid sample using Neu5Ac as an antigen target;
    (b) determining the amount of anti-Neu5Gc antibodies present in the fluid sample using Neu5Gc as an antigen target; and
    (c) subtracting the amount of anti-Neu5Ac antibodies from the amount of anti-Neu5Gc antibodies to determine the amount of anti-Neu5Gc specific antibodies.

2. The method of claim 1, wherein the fluid sample is obtained from a food sample.

3. The method of claim 2, wherein the food sample is a red meat or a dairy product.

4. The method of claim 2, further comprising the step of calculating the Neu5Gc content per serving by multiplying the amount of Neu5Gc in step (b) by a food serving size of a given weight.

5. The method of claim 1, wherein the fluid sample is a clinical sample.

6. The method of claim 5, wherein the clinical sample is from an animal source.

7. The method of claim 6, wherein the clinical sample is urine, tissue, blood or saliva.

8. The method of claim 7, wherein the tissue is suspected of being diseased.

9. The method of claim 5 further comprising the step of repeating steps (a) to (c) at more than one time period.

10. The method of claim 9, wherein the clinical sample is from a human or non-human animal subject, and wherein the subject undergoes a dietary change or therapy during the time period.

11. The method of claim 1, wherein step (a) and step (b) are performed in identical system.

12. The method of claim 11, wherein the fluid sample is a clinical sample.

13. The method of claim 12, wherein the clinical sample is from a human subject.

14. The method of claim 13, wherein the clinical sample is blood.

\* \* \* \* \*

UNITED STATES PATENT AND TRADEMARK OFFICE
CERTIFICATE OF CORRECTION

PATENT NO.         : 7,682,794 B2
APPLICATION NO.    : 10/565742
DATED              : March 23, 2010
INVENTOR(S)        : Ajit Varki, Pam Tangvoranuntakul and Pascal Gagneux Page 1 of 1

It is certified that error appears in the above-identified patent and that said Letters Patent is hereby corrected as shown below:

On the cover page item (75), should read:

Ajit Varki
    Pam Tangvoranuntakul
    Pascal Gagneux

Signed and Sealed this
Fifteenth Day of November, 2011

David J. Kappos
*Director of the United States Patent and Trademark Office*